United States Patent [19]

Fogt

[11] Patent Number: 4,600,495
[45] Date of Patent: Jul. 15, 1986

[54] FLOW THROUGH ION SELECTIVE ELECTRODE

[75] Inventor: Eric J. Fogt, Maple Grove, Minn.

[73] Assignee: Medtronic, Inc., Minneapolis, Minn.

[21] Appl. No.: 765,757

[22] Filed: Aug. 15, 1985

Related U.S. Application Data

[62] Division of Ser. No. 519,934, Aug. 3, 1983, Pat. No. 4,565,665.

[51] Int. Cl.$^4$ ............................................. G01N 27/46
[52] U.S. Cl. ................................... 204/409; 128/635; 204/414; 204/418
[58] Field of Search ............... 204/414, 416, 418, 419, 204/417, 409; 128/635

[56] References Cited

U.S. PATENT DOCUMENTS

| | | | |
|---|---|---|---|
| 2,510,262 | 6/1950 | Sollner et al. | 204/418 |
| 2,614,976 | 10/1952 | Patnode et al. | 204/435 |
| 3,492,216 | 1/1970 | Riseman et al. | 204/419 |
| 3,707,455 | 12/1972 | Derr et al. | 204/419 X |
| 3,879,279 | 4/1975 | Baucke | 204/435 |
| 3,911,901 | 10/1975 | Neidrach et al. | 204/414 X |
| 3,957,612 | 5/1976 | Niedrach et al. | 204/414 |
| 4,105,509 | 8/1978 | Jungck | 204/414 X |
| 4,168,219 | 9/1979 | Hiiro et al. | 204/418 |
| 4,233,136 | 11/1980 | Spaziani et al. | 204/414 |
| 4,242,191 | 12/1980 | Schindler et al. | 204/418 |
| 4,263,115 | 4/1981 | Kessler et al. | 204/415 |
| 4,271,002 | 6/1981 | Hawkins | 204/418 |
| 4,287,042 | 9/1981 | Ebdon et al. | 204/418 |
| 4,314,895 | 2/1982 | Spaziani et al. | 204/418 |
| 4,340,615 | 7/1982 | Goodwin et al. | 204/414 X |
| 4,409,088 | 10/1983 | Kanno et al. | 204/409 |
| 4,486,290 | 12/1984 | Calahan et al. | 204/418 |
| 4,519,973 | 5/1985 | Calahan et al. | 204/409 |

FOREIGN PATENT DOCUMENTS

| | | | |
|---|---|---|---|
| 0015075 | 9/1980 | European Pat. Off. | 128/635 |
| 1593269 | 11/1976 | United Kingdom . | |
| 1593270 | 11/1977 | United Kingdom . | |

OTHER PUBLICATIONS

"Coated Wire Ion Selective Electrodes", by James et al., Analytical Chemistry, vol. 44, No. 4, Apr. 1972—pp. 856–857.

Primary Examiner—John F. Niebling
Assistant Examiner—Terryence Chapman
Attorney, Agent, or Firm—Reed A. Duthler; Joseph F. Breimayer; John L. Rooney

[57] ABSTRACT

An improved flow through ion sensing electrode and a method for producing it. The electrode is formed of bilumen plastic tubing using one lumen as the sample path and the other lumen as a sensing chamber. By permeating a portion of the tubing with an ion selective material, an ion selective membrane integral with the chamber wall is produced. A preferred embodiment also incorporates a reference electrode.

2 Claims, 7 Drawing Figures

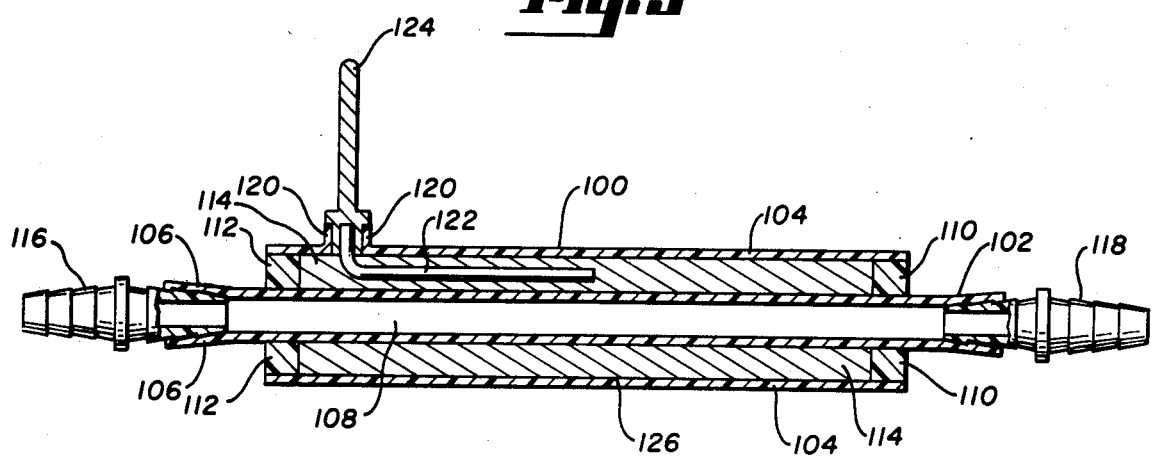
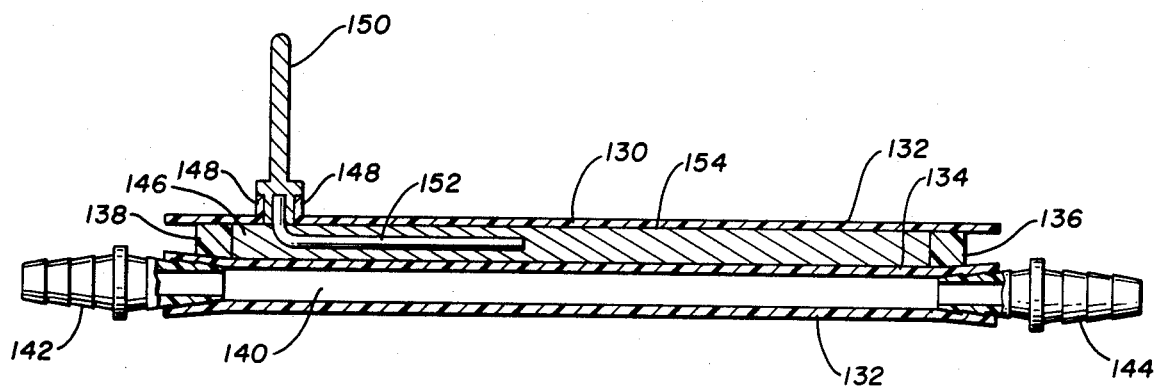
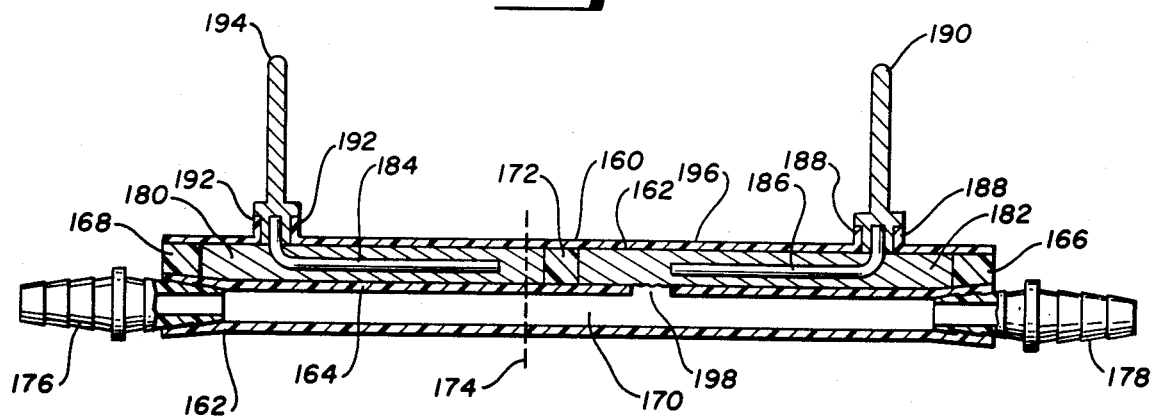

FLOW THROUGH ION SELECTIVE ELECTRODE

CROSS REFERENCE TO RELATED PATENTS AND APPLICATIONS

The subject matter of the present invention is related to co-pending commonly assigned application Ser. No. 632,519 by Cahalan et al, entitled "METHOD OF PRODUCING COMBINATION ION SELECTIVE SENSING ELECTRODE", filed on Aug. 3, 1983 and is related to the following commonly assigned patents: U.S. Pat. No. 4,486,290 issued to Cahalan et al for "COMBINATION ION SELECTIVE SENSING ELECTRODE" and U.S. Pat. No. 4,519,973 issued to Cahalan et al for "ION SELECTIVE MEMBRANES FOR USE IN ION SENSING ELECTRODES".

BACKGROUND OF THE INVENTION

This invention relates to electrodes for measuring ion concentrations in aqueous solutions and to methods of manufacturing such electrodes and the ion-selective membranes they employ.

Ion-sensing electrodes selectively responsive to ionic activities in aqueous solutions are well known to the art. The known relationship between ionic activity and ion concentration permits these electrodes to be used to measure ion concentrations. In such electrodes, selective ion exchange occurs through an interface between a selective ion exchange material and the solution to be sampled. Many recent electrode designs have employed ion-selective membranes which retain the ion-selective material in a matrix of organic material such as polyvinylchloride or other plastic.

Many prior art sensing membranes employing a plastic matrix are prepared by dissolving the ion-selective material in a solvent which either is, or has dissolved within it a plasticizer for the plastic. The plastic, in powdered form, is added to this mixture. The membrane is cast in its desired form by applying this mixture to a substrate having the desired shape and evaporating the solvent or otherwise curing the mixture. Examples of such electrodes are described in U.S. Pat. No. 3,450,631 issued to Bloch, et al, U.S. Pat. No. 3,635,212, issued to Watanabe, U.S. Pat. No. 4,271,002 issued to Hawkins and U.S. Pat. No. 4,242,191 issued to Schindler et al.

In some prior art electrodes, the substrate on which the ion-selective membrane is formed is incorporated as part of the electrode structure. In others, the membrane is removed from the substrate and attached to the body of the electrode. In such electrodes, sealing of the membrane to the remainder of the electrode structure has been problematic.

U.S. Pat. No. 4,233,136 issued to Spaziani, et al, addresses the problem of sealing the ion-selective membrane to the remainder of the electrode structure, in the context of incorporating an ion-selective membrane in the wall of a plastic tube. This method, like that of the prior art electrodes discussed above, involves dissolving powdered plastic in a volatile solvent containing a plasticizer and an ion-selective material and evaporating the solvent to form the membrane. In the Spaziani electrode, a plastic tube is provided with a lateral opening, and a cylindrical mandrel is inserted in the tube across the opening. The mixture is applied to the mandrel, filling the opening of the tube. The volatile solvent fuses the membrane to the plastic tube. After the membrane has formed, the mandrel is removed leaving the membrane in place.

SUMMARY OF THE INVENTION

The present invention includes a novel method of producing an ion-selective membrane and a novel method of producing an ion-sensing electrode employing an ion-selective membrane of a desired shape. The method for producing an ion selective membrane comprises soaking a plastic member of the desired shape in a solution of an ion-selective material dissolved in a volatile solvent which is a swelling agent for the plastic of which the member is fabricated, and drying the member to remove the solvent. By this method, a tubular structure including an ion-selective membrane, for example, may more easily be produced. This method has as a major advantage that it allows the use of preformed, commercially available plastic products, such as single and bi-lumen tubing, to easily and simply fabricate a variety of ion-sensing electrodes. Because the plastic member is first formed to the desired shape and subsequently treated to transform a portion of the member into an ion-selective membrane, the membrane is continuous with and integral to the member, and the problem of sealing the membrane to the electrode can be avoided. Further, because this method does not require use of a substrate to form the ion-selective membrane, production of the membrane in any desired shape is substantially simplified.

The present invention also includes the use of the above process to fabricate ion-sensing electrodes from commercially available plastic members. The methods of fabricating these electrodes are substantially simplified as compared to the methods used to fabricate prior art electrodes. In addition, electrodes formed using the methods set forth herein are believed superior to prior art electrodes in that their ion-selective membranes are integral to the electrode structures.

One preferred embodiment of an electrode according to the present invention uses single lumen polymer tubing to produce a simple ion-sensing electrode. Other preferred embodiments employ bi-lumen tubing to produce combination ion-sensing and reference electrodes adapted to be dipped into the sample solution. Yet other preferred embodiments employ bi-lumen tubing to easily produce ion-sensing and combination-sensing and reference flow through electrodes. The present invention allows all of the described embodiments to be easily produced relative to prior art electrodes. In addition, each described embodiment has unique and valuable features that are described in detail below.

BRIEF DESCRIPTION OF THE DRAWINGS

FIG. 5 shows a flow-through ion-sensing electrode employing a tubular membrane according to the present invention.

FIG. 6 shows an alternate flow-through ion-sensing electrode employing a membrane according to the present invention, fabricated of a bi-lumen tube.

FIG. 7 shows a combination flow-through electrode employing a membrane according to the present invention, also fabricated of a bi-lumen tube.

DETAILED DESCRIPTION OF THE DRAWINGS

Figure 1:
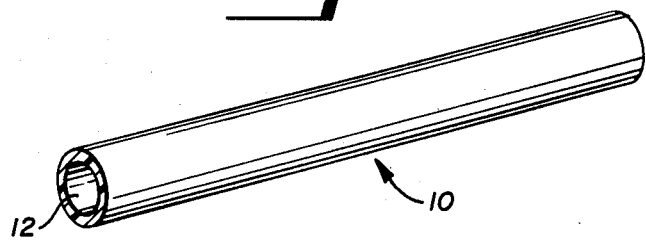
FIG. 1 shows a tubular plastic member, appropriate for use to produce an ion-selective membrane according to the present invention.

FIG. 1 shows a tubular plastic member 10 having lumen 12, appropriate for use in fabricating an ion-selective membrane according to the method of the present invention. Member 10 may be fabricated of silicone rubber, polyvinylchloride, polyurethane, or other swellable plastic. In order to transform member 10 into an ion-selective membrane, the following steps must be performed. First, member 10 must be soaked in whole or in part in a solvent in which the desired ion-selective material has been dissolved and which acts as a swelling agent for the plastic of which member 10 is constructed. Soaking should continue until member 10 has swelled, indicating incorporation of the ion-selective material. Subsequently, the solvent is removed, leaving behind the ion-selective material and allowing the swelling of member 10 to subside. Preferably, the solvent used should be volatile so that it may be conveniently removed by evaporation.

Figure 2:
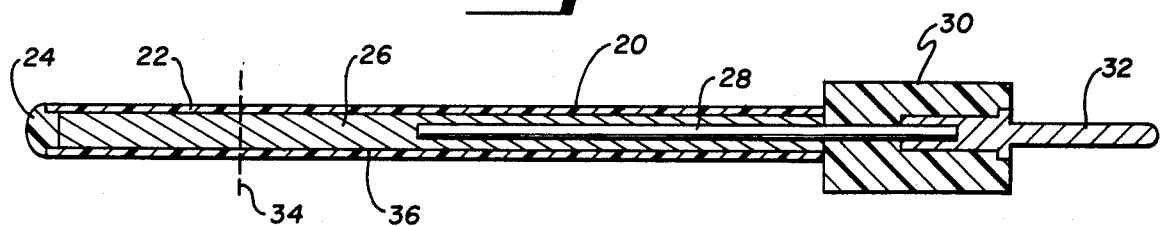
FIG. 2 shows an ion-sensing electrode incorporating an ion-selective membrane fabricated of the member of FIG. 1.

FIG. 2 illustrates a side cross sectional view of an ion-sensing electrode according to the present invention. The ion-selective membrane of the electrode is fashioned from plastic tube 20, which has outer wall 22 impregnated with an ion-selective material, as described above. The lumen 36 of tube 20 is filled with an electrolyte solution or gel 26. The distal end of tube 20 is sealed with plug 24, which may be made of silicone rubber or other suitable material. The proximal end of tube 20 is sealed by connector block 30, which may be made of epoxy or other suitable material. Mounted within connector block 30 is connector pin 32 which is crimped to the proximal end of electrode 28. Electrode 28 may be a silver/silver chloride reference electrode, well known to the art. Connector pin 32 may be made of any conductive metal such as stainless steel. Electrolyte 26 may be any suitable electrolyte solution or gel containing chloride ion and the ion to be detected.

The above electrode is easily fashioned by first treating tube 20 as discussed in conjunction with FIG. 1 above. The entire tube may be treated, or only a portion. For example, only the portion distal to dotted line 34, may be dipped in the solvent. Following evaporation of the solvent, electrolyte 26 should be added. The additional steps of inserting electrode 28 and plug 24 and attaching connector block 30 and pin 32, may be performed in any convenient order, and may preceed the impregnation of tube 20 with the ion-selective material. Because the electrolyte chamber for the sensing electrode is fashioned integrally with the ion-selective membrane, production of the electrode of FIG. 2 is considerably simplified as compared to the prior art.

The effectiveness of ion-selective membranes and ion-sensing electrodes according to the present invention is demonstrated by the following examples:

EXAMPLE 1

A membrane selective for the ammonium ion ($NH_4^+$) was produced as follows:

Silicone rubber tubing of the type manufactured by Dow-Corning Chemical Co., commercially available under the trademark Silastic ® was soaked in a solution of 10 mg of ammonium ion-selective material, Nonactin, an antibiotic, availabe from Sigma Chemical Co. of St. Louis, Mo., dissolved in 2.3 ml of methylene chloride, until the tubing swelled. The tubing was removed from the solution and allowed to dry until it returned to its original dimensions. Three such ammonium ion-selective membranes were incorporated in ion-sensing electrodes as illustrated in FIG. 2. The ion-sensing electrodes were placed in aqueous solutions having known molar concentrations of ammonium ions, along with a reference electrode, and the voltage differences between the reference and sensing electrodes were observed. The correlation of the known molarities of the ammonium ion with the measured voltage differences, illustrated in Table 1, indicates that the ion-sensing electrodes were effective for their intended use.

TABLE 1

| Molarity $NH_4^+$ (M) | Measured Voltages | | |
|---|---|---|---|
| | Electrode 1 (mV) | Electrode 2 (mV) | Electrode 3 (mV) |
| .1 | 150.1 | 148.7 | 140.1 |
| .01 | 97.3 | 94.5 | 87.8 |
| .001 | 43.9 | 44.9 | 34.5 |
| E° | 203.7 | 199.8 | 193.1 |
| slope | 53.1 | 51.9 | 53.3 |
| r | 1.0000 | 0.9997 | 1.000 |

EXAMPLE 2

A membrane selective for potassium ion ($K^+$) was produced as follows:

A length of polyvinylchloride tubing was soaked in a solution of 10 mg of the potassium ion-selective material valimomycin dissolved in 2.5 ml dipentyl phthalate (DPP) available from Eastman Kodak Chemical Co., until the tubing swelled. The tubing was removed and dried for 16 hours at 70° C. Two such potassium ion-selective membranes were incorporated in ion-sensing electrodes as illustrated in FIG. 2. The ion-sensing electrodes were placed in solutions having known concentrations of potassium ions, along with reference electrodes. The voltage differences between the ion-sensing electrodes and the reference electrodes, illustrated in Table 2, indicate that the ion-sensing electrodes were effective for their intended use.

TABLE 2

| Molarity $K^+$ (M) | Measured Voltages | |
|---|---|---|
| | Electrode 1 (mV) | Electrode 2 (mV) |
| $1.0 \times 10^{-3}$ | −68.0 | −71.6 |
| $4.0 \times 10^{-3}$ | −32.1 | −37.4 |
| $6.0 \times 10^{-3}$ | −22.2 | −26.5 |
| E° | 109.2 | 101.3 |
| slope | 59.1 | 57.7 |
| r | 0.9999 | 0.9999 |

A similar procedure was used to fabricate potassium selective membranes from polyurethane tubing.

EXAMPLE 3

A membrane selective for the potassium ion ($K^+$) was produced as follows:

A length of tubing extruded from the polyurethane available under the trade designation Pellathane ®, from Upjohn, was soaked in a solution of 10.0 mg valimomycin and approximately 0.1 mg potassium tetraphenyl borate dissolved in 2.0 ml acetone until the tubing swelled. The tubing was removed from the solution and allowed to dry until the tubing returned to its original dimensions. Two such potassium ion-selective membranes were incorporated in ion-sensing electrodes as illustrated in FIG. 2. The ion-sensing electrodes along with a reference electrode were placed in an aqueous solution having a known molar concentration of potassium ions, to which known increments of a 0.1 M potassium solution were added, and the voltage differences between the reference and sensing electrodes were observed. The correlation of the known molarities of the potassium ions with the measured voltage differences, illustrated in Table 3, indicates that the ion-sensing electrodes were effective for their intended use.

TABLE 3

| Molarity $K^+$ (M) | Measured Voltages | |
|---|---|---|
| | Electrode 1 (mV) | Electrode 2 (mV) |
| $9.9 \times 10^{-4}$ | −44.9 | −41.0 |
| $2.0 \times 10^{-3}$ | −32.9 | −29.9 |
| $3.8 \times 10^{-3}$ | −20.1 | −17.2 |
| $5.7 \times 10^{-3}$ | −12.2 | −9.6 |
| $9.1 \times 10^{-3}$ | −2.7 | −0.8 |
| $1.2 \times 10^{-2}$ | +3.2 | +4.2 |
| E° | 92.9 | 89.5 |
| slope | 44.3 | 42.0 |
| r | 0.9998 | 0.9998 |

EXAMPLE 4

A membrane selective for the chloride ion (Cl⁻) was produced as follows:

A length of silicone rubber tubing as described in Example 1, above, was soaked in a solution of one part by volume of the chloride ion-selective material methyl tricapryl ammonium chlroide, commercially available from General Mills Co. under the trade designation Aliquat ® to two parts by volume of Xylene. The tubing was soaked for about one day and then vacuum dried. The Xylene was found to come off easily, but a surface residue of Aliquat remained which was removed by washing with additional Xylene. Two such membranes were incorporated in ion-sensing electrodes as illustrated in FIG. 2. These sensing electrodes were placed in aqueous solutions having known concentrations of chloride ion, and tested as described in Examples 1 and 2 above. The results, illustrated in Table 4, indicate that the ion-sensing electrodes were effective for their intended use.

TABLE 4

| Molarity Cl⁻ (M) | Measured Voltages | |
|---|---|---|
| | Electrode 1 (mV) | Electrode 2 (mV) |
| .1 | 55.9 | 81.5 |
| .01 | 99.4 | 128.8 |
| .001 | 137.8 | 169.8 |
| E° | 15.8 | 38.9 |
| slope | −40.9 | −44.2 |
| r | .9994 | .9992 |

EXAMPLE 5

A membrane appropriate for use in a pH sensing electrode was produced as follows:

A length of silicone rubber tubing as described above was soaked in a solution of one part by volume of tridodecylamine to two parts by volume of Freon until the tubing swelled. The tube was allowed to air dry until it returned to its original dimensions. Three such membranes were incorporated in ion sensing electrodes as illustrated in FIG. 2, using a pH4 buffer containing NaCl as an electrolyte. These pH sensing electrodes were placed in solutions having known pH, and tested as described in the examples above. The results, illustrated in Table 5, indicate that the ion-sensing electrodes were effective for their intended use.

TABLE 5

| pH | Measured Voltages | | |
|---|---|---|---|
| | Electrode 1 (mV) | Electrode 2 (mV) | Electrode 3 (mV) |
| 6 | −133.3 | −132.1 | −144.6 |
| 7 | −190.8 | −184.8 | −189.8 |
| 8 | −241.6 | −240.5 | −242.8 |
| E° | 190.1 | 193.6 | 151.3 |
| slope | 54.1 | 54.2 | 49.1 |
| r | .9996 | .9949 | .9990 |

Figure 3:
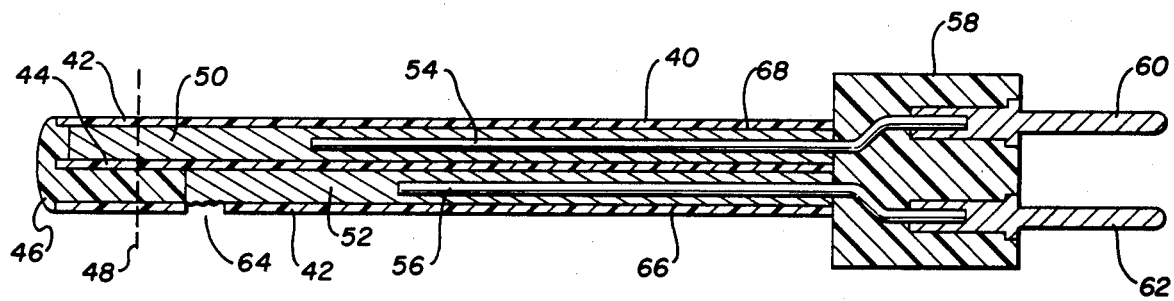
FIG. 3 shows a combination electrode employing a membrane according to the present invention, fabricated of a bi-lumen tube.

FIG. 3 illustrates a side sectional view of a combination ion-sensing and reference electrode according to the present invention. The ion-selective membrane is fashioned from bi-lumen plastic tube 40, of which the portion distal to dotted line 48 is impregnated with an ion-selective material, using the process described above. The first lumen 68 of tube 40 is filled with electrolyte 50, and acts as the electrolyte chamber for the ion-sensing electrode. Second lumen 66 is filled with electrolyte 52, and acts as the electrolyte chamber for the reference electrode. Electrolyte 52 is exposed to the sample solution via aperture 64. The distal ends of lumens 66 and 68 are sealed by plug 46 which may be made of silicone rubber or other suitable material. The proximal ends of lumens 66 and 68 are sealed by connector block 58, which may be made of epoxy or other suitable material. Mounted within connector block 58 are connector pins 60 and 62, which are crimped to the proximal ends of electrodes 54 and 56. Electrodes 54 and 56 may be silver/silver chloride reference electrodes, well known to the art. Connector pins 60 and 62 may be made of any conductive metal such as stainless steel. Electrolytes 50 and 52 should contain silver and chloride ions, along with the ion to be detected. Because electrolyte 52 is exposed to the sample solution, it is desirable that it be a gel electrolyte. A preferred gel is discussed below.

The above electrode is fashioned by treating tube 40, distal to dotted line 48, as discussed in conjunction with FIG. 1 above, by dipping the distal end of tube 40 into the solvent. Following evaporation of the solvent, electrolyte 50 and 52 should be added. The additional steps of inserting electrodes 54 and 56, attaching connector block 58, attaching connector pins 60 and 62, inserting plug 46, and forming aperture 64 may be performed in any convenient order, and may preceed the impregnation of tube 40 with the ion-selective material. Aperture 64 may be produced by simply placing a hole in a portion of outer tube wall 42, opening lumen 66 to the exterior of tube wall 42 and allowing free migration of ions from the solution to be tested into electrolyte 52. It is important to note that aperture 64 is located proximal to dotted line 48, and that plug 46 extends proximal to dotted line 48, thereby providing a seal intermediate the electrolyte contained within lumen 66 and the portion of tube 40 which has been impregnated with the ion-selective material. The seal is desirable to prevent migration of ions between the lumens which would interfere with the efficiency of the electrode. Because the electrolyte chambers for both the sensing electrode and the reference electrode are fashioned integrally with the ion-selective membrane, production of the electrode of FIG. 3 is considerably simplified as compared to the prior art.

EXAMPLE 6

A combination potassium slective electrode and reference electrode was produced as folows:

A length of bi-lumen silicone rubber tubing was soaked in a solution of 10 mg valinomycin and 2.5 ml of Xylene until the tubing swelled. The tubing was removed from the solution and allowed to dry until the tubing returned to its original dimensions. Combination electrodes as illustrated in FIG. 3 were fabricated from this tubing. The combination electrodes were placed in aqueous solutions having known molar concentrations of potassium ions, and the voltage differences between the potassium sensing electrode and the reference electrode were observed. The correlation of the known molarities of the potassium ion with the measured voltage differences, illustrated in Table 6 indicates that the combination electrodes were effective for their intended use:

TABLE 6

| Molarity $K^+$ (M) | Measured Voltages | | |
|---|---|---|---|
| | Electrode 1 (mV) | Electrode 2 (mV) | Electrode 3 (mV) |
| $1 \times 10^{-3}$ | −152.1 | −108.6 | −118.4 |
| $4 \times 10^{-3}$ | −117.7 | −74.3 | −84.1 |
| $6 \times 10^{-3}$ | −108.2 | −64.0 | −74.6 |
| E° | 38.9 | 5.8 | 5.4 |
| slope | 56.7 | 57.2 | 56.5 |
| r | 0.9999 | 0.9999 | 0.9999 |

Figure 4:
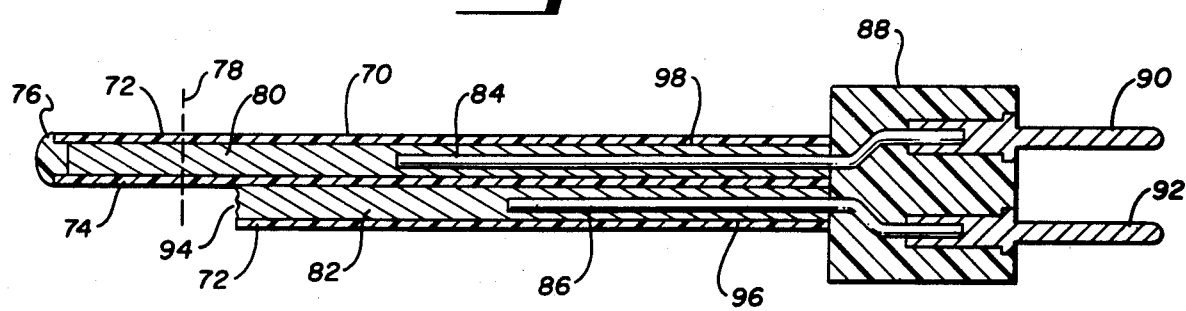
FIG. 4 shows an alternative combination electrode, also employing a membrane according to the present invention, fabricated of a bi-lumen tube.

FIG. 4 illustrates a side sectional view of a combination ion-sensing and reference electrode according to the present invention. Like the electrode of FIG. 3, this electrode is fashioned from a bi-lumen plastic tube 70. That portion of tube 70 which is distal to dotted line 78 is impregnated with an ion-selective material.

Only the distal end of lumen 98, which serves as the electrolyte chamber for the ion-sensing electrode, is sealed by means of plug 76, which may be made of silicone rubber or other suitable plastic. The distal end of lumen 96 remains open to the exterior of tube 70, via aperture 94. Lumen 96 serves as the electrolyte chamber for the reference electrode portion. Electrodes 84 and 86, connector block 88, and connector pins 90 and 92 are identical to the corresponding elements in FIG. 3, above.

The above electrode is fashioned by treating bi-lumen tube 70 distal to dotted line 78 as discussed in conjunction with FIG. 1 above. This may be accomplished by dipping only that portion of tube 70 distal to dotted line 78 in the solvent. Following the evaporation of the solvent, electrolyte 80 and 82 should be added. Electrolyte 80 and 82 correspond to electrolyte 50 and 52 of FIG. 3. The additional steps of inserting electrodes 84 and 86, attaching connector block 88, inserting plug 76 and attaching connector pins 90 and 92, may be performed in any convenient order, and may proceed the impregnation of tube 70 with the ion-selective material. It is important to note that lumen 96 does not extend distal to dotted line 78. As such, no portion of inner wall 74 which is impregnated with the ion-selective material, is exposed to lumen 96, preventing transfer of ions between lumens. Bi-lumen tube 70 may be conveniently fabricated by removing a portion of the outer tube wall surrounding lumen 96, intermediate the distal end of tube 70 and a point proximal to dotted line 78. Because the electrolyte chambers for both the sensing and reference electrodes are fashioned integrally with the ion-selective membrane, production of the electrode of FIG. 4 is considerably simplified as compared to the prior art. Further, the removal of a portion of the outer wall, surrounding lumen 96 to prevent selective ion transfer between lumens 96 and 98 is believed to be both easier to accomplish and more effective than the structure of FIG. 3, which requires that plug 46 tightly seal lumen 66 distal to aperture 64. Leakage of this seal could result in selective ion transfer between lumens 68 and 66. There is no corresponding seal in the structure of FIG. 4, and possibilities of malfunction of the electrode due to seal leakage are therefore believed to be reduced.

FIG. 5 illustrates a side sectional view of a flow through ion-sensing electrode. The ion-selective membrane of the electrode is fashioned from plastic tube 102, which has outer wall 106 impregnated with an ion-selective material, as described above. Tube 102 also serves as the sample tube for the electrode. Located coaxially around tube 102 is outer tube 100, which may be conveniently made of any appropriate plastic. The proximal and distal ends of tube 100 are sealed around tube 102 by means of sealing disks 110 and 112, respectively. That portion of lumen 126 of tube 100 intermediate tube wall 104 of tube 100 and tube wall 106 of tube 102 is filled with electrolyte 114. Electrolyte 114 corresponds to electrolyte 26 of FIG. 2. The proximal and distal ends of tube 102 are coupled to fluid couplings 118 and 116, respectively. Fluid couplings 116 and 118 may be any appropriate fluid couplings adapted for use with plastic or rubber tubing. Electrode 122 and connector pin 124 are identical to the corresponding elements in the Figures above. Securing connector pin 124 to tube 100 is tubular sleeve 120, which may be fashioned of an appropriate plastic or other material.

The above electrode is fashioned by first treating tube 102 as discussed in conjunction with FIG. 1 above. The entire tube, or only a portion may be treated. Following evaporation of the solvent, tube 100 and sealing disks 110 and 112 are added. The electrolyte 114 may then be conveniently added, however, there is no criticality in the order of the steps. The steps of inserting electrode 122 and attaching connector pin 124 and tubular sleeve 120 are similarly not critical to the manufacture of this device. Because the sensing membrane is formed integrally with the sample tube of the flow through electrode, production of the electrode of FIG. 5 is considerably simplified as compared to the prior art.

FIG. 6 illustrates a side sectional view of a preferred embodiment of a flow-through ion-sensing electrode according to the present invention. The ion-selective membrane of the electrode is fashioned from bi-lumen polymer plastic tube 130, which has at least inner wall 134 impregnated with an ion-selective material, as described above. Lumen 154 of tube 130 is filled with electrolyte 146, which corresponds to electrolyte 26 of FIG. 2. Sealing the proximal and distal ends respectively of lumen 154 are plugs 136 and 138, which may be conveniently fashioned of silicone rubber or other suitable material. Lumen 140 of tube 130 serves as the sample tube for the electrode. Coupled to the proximal and distal ends of lumen 140 are fluid couplings 142 and 144 respectively. Fluid couplings 142 and 144 are identical to the corresponding structures shown in FIG. 5. Electrode 152, connector pin 150, and tubular sleeve 148 correspond to the identically named structures in FIG. 5 above.

The above electrode is fashioned by first treating a bi-lumen tube 130 as discussed in conjunction with FIG. 1 above. The entire tube may be treated, or only a portion thereof. Following the evaporation of the solvent, electrolyte 146 should be added. The additonal steps of inserting plugs 136 and 138, inserting electrode 152, attaching circular sleeve 148 and connector pin 150, and inserting fluid couplings 142 and 144 may be performed in any convenient order, and may preceed the impregnation of tube 130 with the ion-selective material. Because the electrolyte chamber and the sample tube of this electrode are fashioned integrally with the ion-selective membrane, production of the electrode of FIG. 6 is considerably simplified as compared to prior art electrodes.

FIG. 7 illustrates a side sectional view of a combination of ion-sensing and reference flow-through electrodes according to the present invention. The ion-selective membrane of the electrode is fashioned from bi-lumen plastic tube 160, of which at least inner wall 164 is impregnated with an ion-selective material, distal to dotted line 174. The proximal and distal ends of lumen 196 of tube 160 are sealed by means of plugs 166 and 168 respectively. In addition, lumen 196 is sealed centrally by means of plug 172. The portion of lumen 196 distal to plug 172 serves as the electrolyte chamber for the ion-sensing electrode. That portion of lumen 196 located proximal to plug 172 serves as the electrolyte chamber for the reference electrode. Inner wall 164 is provided with aperture 198, exposing electrolyte 182 to lumen 170, which serves as the sample tube for the electrode. Electrolyte 180 and 182 correspond to electrolyte 50 and 52 of FIG. 3. Coupled to the proximal and distal ends of lumen 170 are fluid couplings 178 and 176, respectively, which are identical to the corresponding structures in FIGS. 5 and 6. Similarly, electrodes 184 and 186, tubular sleeves 192 and 188, and connector pins 190 and 194 are identical to the corresponding structures having the same names in FIGS. 5 and 6.

The above electrode is fashioned by treating a bi-lumen tube 160 as discussed in conjunction with FIG. 1 above. Only the portion of the tube distal to dotted line 174 should be impregnated with the ion-selective material. Following evaporation of the solvent, electrolyte 180 and 182 should be inserted in lumen 196. The additional steps of inserting plugs 166, 168 and 172, fluid couplings 176 and 178, connector pins 190 and 194, circular sleeves 188 and 192, and electrodes 184 and 186, along with the step of cutting aperture 198, may be performed in any convenient order and may proceed the impregnation of tube 160 with the ion-selective material. Because the electrolyte chambers for both the sensing and reference electrodes of the present invention, along with the sample tube, are all constructed integrally with the ion selective membrane, production of the electrode of FIG. 7 is considerably simplified as compared to the prior art. It is important to note that seal 172 is located proximal to dotted line 174, so that ion transfer between the sensing and reference chambers is precluded.

With regard to the electrodes of FIGS. 6 and 7, the construction of such electrodes, using commercially available bi-lumen plastic tubing provides the opportunity for arranging any number of ion-sensing and reference electrodes within a single unified tubular structure. Such a multiple electrode structure is believed within the scope of the present invention.

An electrolyte gel appropriate for use in all of the above embodiments, but especially useful in the embodiments of FIGS. 3, 4 and 6, may comprise a polyvinyl alcohol gel comprising (by weight) 7% polyvinylalcohol, 92.5% water, and 0.5% concentrated (18M) sulfuric acid as a polymerizing agent. The gel should be saturated with silver chloride, and be provided with electrolytes including the ion to be sensed. For example, electrolyte levels of 0.15M NaCl and 0.1 MKCl would be appropriate in a chloride ion sensing electrode. The gel may be stabilized by including 0.025% (be weight) gluteraldehyde as a cross linking agent. Such a gel is a stable, non-swelling, non-erroding gel, suitable for use with the above described electrodes. In addition, such a gel is capable of withstanding flexing without crumbling. These characteristics are especially desirable in a gel used with the above electrodes, because the gel is exposed directly to the sample solution in the reference electrode portions of the electrodes shown in FIGS. 3, 4, and 7.

Although several embodiments of the invention have been disclosed herein, it will be understood that the embodiments disclosed may be subjected to various changes, modifications and substitutions without departing from the spirit and scope of the invention as defined by the appended claims.

We claim:

1. A flow through ion sensing electrode, comprising:
    a plastic tube having a proximal end, a distal end, an outer wall, a first lumen, a second lumen, and an inner wall separating said first lumen from said second lumen, said second lumen having first and second ends open to the exterior of said electrode, a portion of said tube including at least part of said inner wall impregnated with an ion selective material;
    first sealing means for sealing the first lumen of said tube proximal to at least part of said impregnated portion of said tube;
    second sealing means for sealing the first lumen of said tube distal to at least a portion of said impregnated portion of said tube;
    electrolyte gel filling the first lumen of said tube intermediate said first and second sealing means; and
    first electrode inserted in the first lumen of said tube intermediate said first and second sealing means.

2. An ion sensing electrode according to claim 1 wherein said tube is impregnated with said ion selective material only distal to a first point intermediate the proximal and distal ends of said tube, and wherein the inner wall of said tube is provided with an aperture at a second point proximal to said first point, opening the first lumen of said tube to the second lumen of said tube, and further comprising:
    third sealing means for sealing the first lumen of said tube intermediate said first and second points, and proximal to said first electrode; and
    second electrode inserted in said first lumen intermediate said and third sealing means.

* * * * *